United States Patent [19]

Grim et al.

[11] Patent Number: 5,058,576
[45] Date of Patent: Oct. 22, 1991

[54] ADJUSTABLE WRIST AND HAND SPLINT

[75] Inventors: Tracy E. Grim, Tulsa, Okla.; Fritz F. Gamble, Memphis, Tenn.

[73] Assignee: Royce Medical Company, Westlake Village, Calif.

[21] Appl. No.: 217,988

[22] Filed: Jul. 12, 1988

[51] Int. Cl.$^5$ .............................................. A61F 5/04
[52] U.S. Cl. .................................. 128/87 R; 128/87 A
[58] Field of Search ............... 128/77, 85, 87 R, 87 A, 128/88; 2/16, 20, 162, 163

[56] References Cited

U.S. PATENT DOCUMENTS

| | | | |
|---|---|---|---|
| 770,619 | 9/1904 | Waller | 2/16 |
| 1,227,700 | 5/1917 | Tucker | 128/89 R |
| 2,206,404 | 7/1940 | Jones | 128/89 R |
| 3,269,728 | 8/1966 | Blough | 2/16 |
| 3,408,077 | 10/1968 | Norwood | 128/87 R |
| 3,467,799 | 9/1969 | Kistner | 128/87 R |
| 3,598,408 | 8/1971 | Klose | 273/54 B |
| 3,788,307 | 1/1974 | Kistner | 128/77 |
| 3,938,509 | 2/1976 | Barber | 128/77 |
| 4,013,070 | 3/1977 | Haroff | 128/77 |
| 4,062,073 | 12/1977 | Rhee | 2/16 |
| 4,183,098 | 1/1980 | Knowles, Jr. | 2/16 |
| 4,193,135 | 3/1980 | Rhee | 2/162 |
| 4,382,439 | 5/1983 | Shen | 128/77 |
| 4,384,571 | 5/1983 | Nuzzo et al. | 128/77 |
| 4,400,829 | 8/1983 | Willis | 2/16 |
| 4,441,490 | 4/1984 | Nirschl | 128/77 |
| 4,584,993 | 4/1986 | Nelson | 128/77 |
| 4,677,971 | 7/1987 | Lindemann | 128/87 R |

FOREIGN PATENT DOCUMENTS 3006362  8/1981  Fed. Rep. of Germany ........ 128/77

*Primary Examiner*—Robert A. Hafer
*Assistant Examiner*—Charles H. Sam
*Attorney, Agent, or Firm*—Poms, Smith, Lande & Rose

[57] ABSTRACT

An adjustable wrist and hand splint employs four rigid aluminum stays for providing support for the forearm, fourth and fifth fingers and the outer portion of the hand. The aluminum stays are bendable for accommodating particular needs of the user. The splint also employs a sleeve that encompasses and provides further support for the forearm, fourth and fifth fingers and outer portion of the hand. The sleeve also provides padding between the stays and the forearm, hand and fingers. In addition, the splint includes pockets that are secured to the sleeve. The aluminum stays are housed within the pockets. Further, the splint may be readily put on or removed using a set of adjustable straps. The straps normally include "Velcro" type material that engage the mating "Velcro" type material on the surface of the sleeve. The fastening straps also help to further immobilize the wrist, fourth and fifth fingers and outer portion of the hand.

20 Claims, 2 Drawing Sheets

ADJUSTABLE WRIST AND HAND SPLINT

FIELD OF THE INVENTION

This invention relates to removable hand and wrist splints used when the fourth or fifth metacarpel bone, one of the outside long bones of the hand, is broken, or the fourth or fifth finger is broken.

BACKGROUND OF THE INVENTION

When the long bone of the hand which leads to the little finger is broken, often referred to as a "boxer's fracture", a plaster cast is normally used to tiqhtly encompass a substantial portion of the wrist, hand, and fingers. This cast usually encompasses a substantial portion of the little finger (fifth finger), adjacent finger (fourth finger), palm of the hand and wrist. Therefore, the cast allows little, if any, beneficial use of the hand or fingers. In addition, this cast cannot be removed until total mending of the break. Due to the lack of mobility during this period, the wrist, hand and fingers become substantially weak.

A splint applied to the hand and wrist to assist it in overcoming injury should provide for the maximum mobility of hand and fingers to allow the hand to carry most of the normal functions. Splints possessing such characteristics prevent the wrist and hand from getting substantially weak or stiff. However, too much mobility may cause further pain or injury to the injured bones or joints, and prevent the broken bone from mending. Therefore, a desirable splint should provide for 1) a secure and tight support for the outside long bone of the hand, fourth and fifth fingers and forearm, and 2) beneficial use of the hand and the remainder of the fingers and thumb during the immobilization period. Conventional plaster of paris cast splints allow very little mobility. The lack of mobility disrupts most of the functions of the hand. Further, due to the lack of mobility, the hand and wrist are substantially weakened when in a cast for a long time. Other splints that allow some mobility have failed to provide sufficient support to prevent further pain or injury.

Current wrist and hand splints do not provide the necessary support in the appropriate places or are so bulky that the benefits of using them are greatly diminished. A brief review of the prior art reveals these shortcomings.

The U.S. Pat. No. 4,382,439 to Shen discloses a "thumb spica" for use by persons requiring wrist and hand support. The brace forms a sleeve that provides a longitudinal support for the wrist and hand. Although the wrist and hand are sufficiently supported, the brace fails to support the fourth and fifth fingers. Supporting these fingers is an essential feature of a brace used for the treatment of an injured hand bone which leads to the fourth and fifth fingers. This drawback of the "Shen" patent in failing to adequately support the fourth and fifth fingers and outer portion of the hand is shared by U.S. Pat. No. 1,227,700 to Tucker, U.S. Pat. No. 4,441,490 to Nirschl, U.S. Pat. No. 4,584,994 to Nelson, U.S. Pat. No. 4,183,098 to Knowles, U.S. Pat. No. 3,598,408 to Kloss, U.S. Pat. No. 2,206,404 to Jones, and U.S. Pat. No. 4,677,971 to Lindemann.

Accordingly, a principal object of the present invention is to provide a hand and wrist splint which adequately supports the outside long bone of the hand, the fourth and fifth fingers, and forearm, and which will allow partial use of the hand and full use of the thumb, index, and middle fingers.

SUMMARY OF THE INVENTION

In accordance with the present invention, an orthopaedic soft goods splint assembly for immobilizing the wrist, the fourth and fifth fingers and outer portion of the hand includes, among other elements, a splint means for substantially immobilizing the wrist, fourth and fifth fingers and outer portion of the hand, a sleeve, and fastening means for holding the assembly in place.

The splint assembly includes support means for providing rigid support for the wrist, fourth and fifth fingers and outer portion of the hand. The support means may include a plurality of stiff aluminum stays that support the wrist, fourth and fifth fingers and outer portion of the hand. The aluminum stays are housed within pockets that are secured to the sleeve. The aluminum stays are sufficiently bendable that they may be adjusted or bent to fit the form of the wrist, fourth and fifth fingers and outer portion of the hand. This adjustability is a desirable feature for the stays particularly if both the forearm and fingers are injured and need to be properly supported. The splint may include four stays, having various lengths and bent differently to accommodate the needs of a particular application.

The first stay normally extends from the middle of the forearm to the middle of the palm. For a comfortable and secure support, the first stay may be bent towards the palm of the hand as the stay passes over the pad of the thumb.

The second stay normally extends from the middle of the forearm to the fourth and fifth fingers. The second stay is also normally bent such that the fourth and fifth fingers cup around it. With the fingers cupped around it, the second stay securely supports these fingers and prevents them from moving towards the palm of the hand.

The third stay extends along the back of the forearm to the back of the fourth and fifth fingers. The third stay is bent to cup around the fourth and fifth fingers. With the third stay being cupped around the fourth and fifth fingers, it securely supports these fingers and prevents them from moving away from the palm of the hand.

Finally, the fourth stay extends along the back of the forearm and hand. It is positioned opposite the first stay and bent slightly over the back of the hand, and ends at the middle of the hand.

The splint assembly also includes a flexible soft goods sleeve for at least partially enclosing the forearm and the fourth and fifth fingers. The sleeve encompasses, and provides further support for, the forearm, fourth and fifth fingers and outer portion of the hand. The sleeve also provides a padding between the support means and the forearm and fingers. Further, the sleeve may include two portions attached to each other by a flexible hinge. Normally, one portion of the sleeve includes the first and second stays, while the other portion includes the third and fourth stays. The flexible hinge allows the sleeve to be readily wrapped around the wrist. Normally, the sleeve includes such soft covering as a vinyl covering. The wrist, hand and fingers come in contact with this soft covering when the splint is wrapped around the wrist. The splint assembly may be fastened to the wrist, hand, and fingers using straps, metal loops and Velcro type material, on the surface of the sleeve, that securely engage mating Velcro type material on the surface of the straps. The straps and sleeve contribute to the immobilization of the forearm, fourth and fifth fingers and their radial aspects.

The fastening straps may include a wrist strap, a hand strap, and a finger strap to adjustably fasten the splint to the forearm, hand and fingers, respectively. The straps may include Velcro type material on their surface to securely engage mating "Velcro" type material on the surface of the sleeve, as noted above.

The finger strap is situated between the third and fourth fingers, and helps to further immobilize the fourth and fifth fingers. The hand strap is normally situated between the thumb and second finger, and securely holds the splint to the hand. The forearm straps may include three separate straps for securely holding the splint to the forearm.

In summary, the aluminum stays cooperate to provide a firm support for the forearm, fourth and fifth fingers and the outer portion of the hand. Further, the stays may have varying length and width to accommodate varying degrees of support for the forearm, hand, and fingers. In addition, the stays may be housed within pockets that secure the stays to the sleeve. The sleeve provides for padding between the forearm, hand and fingers and the aluminum stays. The sleeve also provides further support for the injured forearm, hand and fingers. The manner in which the aluminum stays are housed within the pockets provides for a splint that is flexible and may readily encompass the wrist, fourth and fifth fingers and their radial aspects.

The assembly has been informally called an "ulna gutter", as it extends along the ulna side of the forearm and includes a U-shaped configuration which encompasses the two little fingers.

The adjustability of the assembly allows for expansion to accommodate swelling, and the capability of reducing the size of the assembly when the swelling goes down.

Other objects, features and advantages of the invention will become apparent from a consideration of the following detailed description and from the accompanying drawings.

DETAILED DESCRIPTION

Figure 1:
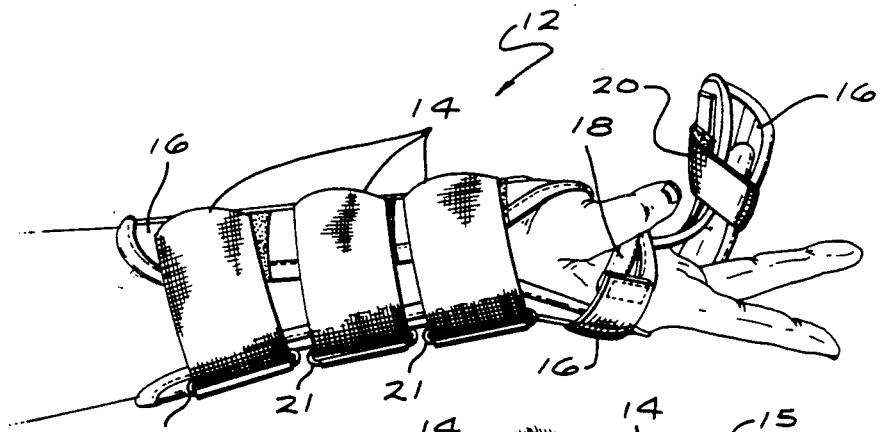
FIG. 1 is a perspective view of the removable orthopaedic splint when applied to the wrist, fourth and fifth fingers and the outer portion of the hand.

Referring more particularly to the drawings, FIG. 1 is a perspective view of a removable orthopaedic splint assembly 12 as applied to the wrist, hand, fourth and fifth fingers. As shown, sleeve 16 supports the forearm, hand, fourth and fifth fingers. Further, straps 14 and 18 enhance this support by securely tightening sleeve 16 around the forearm and hand, respectively. In addition, strap 20 helps to immobilize the fourth and fifth fingers. As shown in FIG. 1, splint assembly 12 achieves our dual goals of 1) providing sufficient support for the forearm, hand and fingers, and 2) allowing maximum possible use of the hand, thumb, index and middle fingers. These dual goals are achieved because, while the forearm, hand and fourth and fifth fingers are substantially immobilized to help recovery, the thumb, middle and index fingers are virtually free to perform such important and routine tasks as writing or driving. Further, to enhance recovery and comfort for the user, the fourth and fifth fingers may be immobilized at any desirable position. Finally, and as shown in FIG. 2, splint 12 is easy to remove and put back on.

Figure 2:
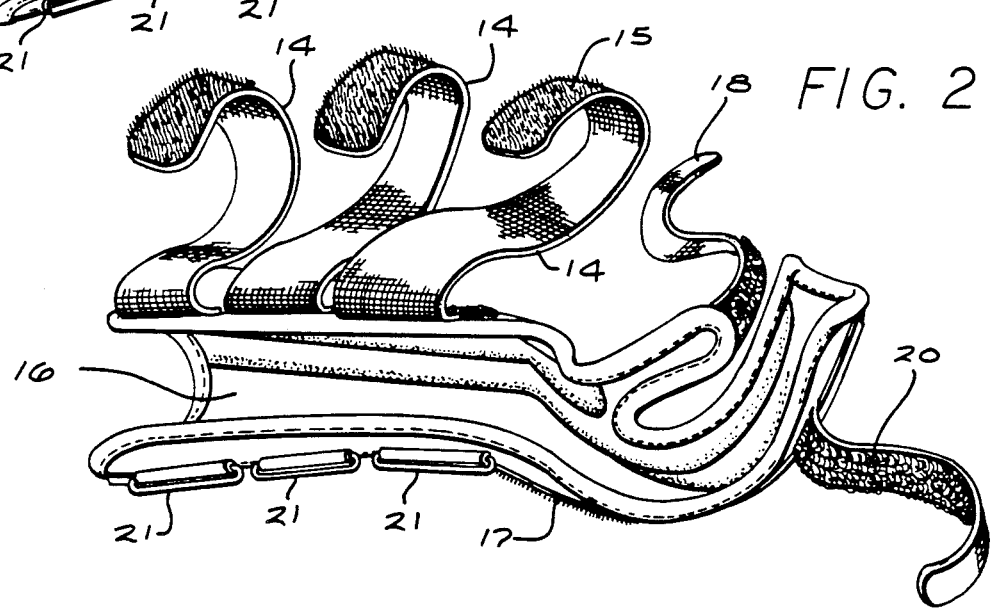
FIG. 2 is a perspective view of the splint of FIG. 1 showing the straps and housing.

FIG. 2 is a perspective view of splint assembly 12 of FIG. 1 showing the straps 14, 18, and 20, and sleeve 16. As shown in FIG. 2, splint 12 may easily be put back on by placing the injured forearm inside the sleeve such that the forearm, hand and fourth and fifth fingers are encompassed within the sleeve 16. Then, the forearm and hand may be secured within sleeve 16 by using straps 14 and 18, respectively. Further, the fourth and fifth fingers may be secured within the sleeve 16 using strap 20. Finally, straps 14, 18 and 20 may include Velcro type material 15 on their surface to accommodate a quick and easy engagement of the straps to the mating Velcro type material 17 secured to the surface of sleeve 16, or to the back of the straps following looping of some of the straps through the metal loops or rings 21.

VELCRO is a trademark, and the products sold under the VELCRO trademark are mating fabric pads, with one of the pads having its surface provided with a fine array of closely spaced outwardly protruding hooks, and the other of the mating pads being outwardly extending loops or other material with which the hooks may engage.

Further, the shape of sleeve 16 may be varied to accommodate the shape of the injured hand. The shape of sleeve 16 may be varied by changing the shape of the supporting aluminum stays partially shown in FIG. 3. FIGS. 5 through 8 display stays, used in a typical splint, having various shapes and sizes. Before discussing the configuration of the individual stays, their application within a typical splint will be reviewed.

Figure 3:
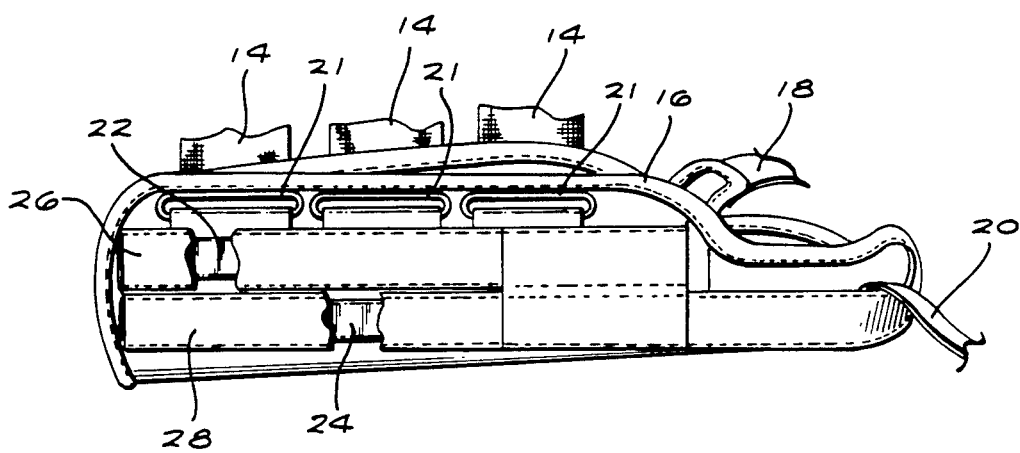
FIG. 3 is a perspective view of the splint with cut-away zones showing a pair of aluminum stays held in pockets.
Figure 7:
Figure 8:
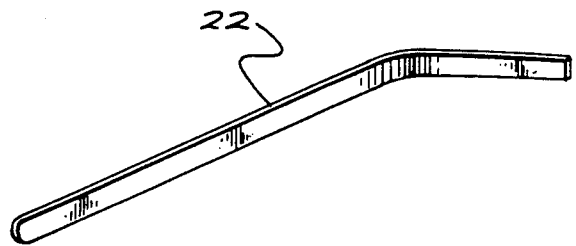

FIG. 3 is a perspective view of splint 12 with portions of the drawing being cut away, thereby showing two aluminum stays 22 and 24. As shown, the aluminum stays 22 and 24 are housed within the designated pockets 26 and 28, respectively, secured to sleeve 16. Normally, stays 22 and 24 support the front of the forearm, hand, fourth and fifth fingers. Stay 22, also shown in FIG. 8, is extended from approximately middle of the forearm to approximately middle of the hand to support the forearm and hand. As shown in FIG. 8, stay 22 is substantially flat throughout the length of the forearm, and is bent slightly over the back of the hand. In addition, stay 24 cooperates with stay 22 to provide further support for the back of the forearm and hand. Stay 24, also shown in FIG. 7, also supports the hand, and the fourth and fifth fingers because it extends along the back of the forearm to the back of the fourth and fifth fingers. As shown in FIG. 7, Stay 24 is substantially flat throughout the length of the forearm and is bent such that it cups around the fourth and fifth fingers.

In summary, stays 22 and 24, in cooperation with sleeve 16, and straps 14, 18, and 20 firmly support the back of the forearm, hand, and fourth and fifth fingers. Similarly, stays 30 and 32, in cooperation with sleeve 16, and straps 14, 18, and 20 firmly support the front of the forearm, hand, and fourth and fifth fingers, as shown in FIG. 4.

Figure 4:
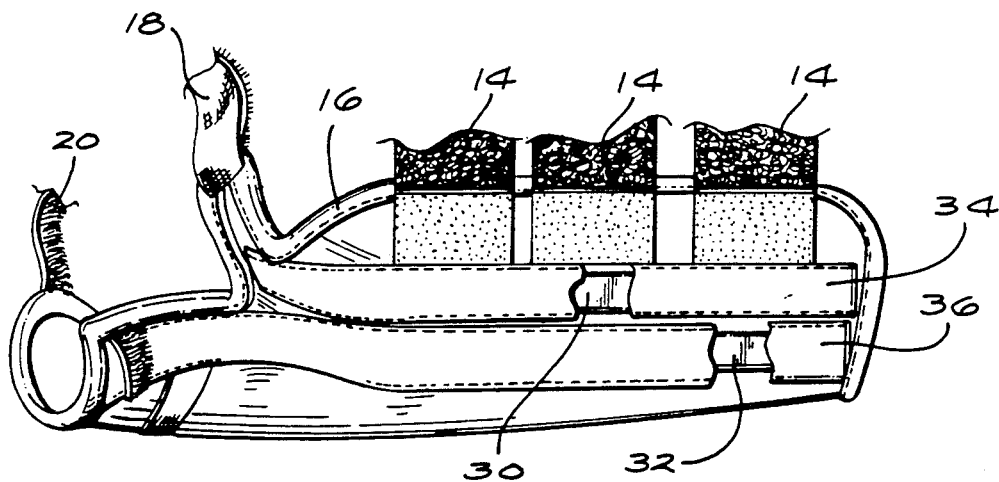
FIG. 4 is a perspective view of the splint with two additional pockets with cut-away areas showing another pair of aluminum stays.
Figure 5:
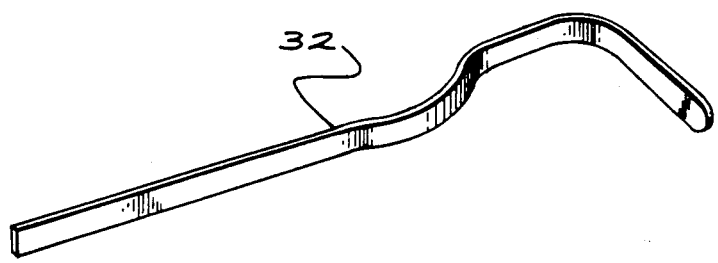
FIGS. 5-8 are perspective views of four different aluminum stays.
Figure 6:
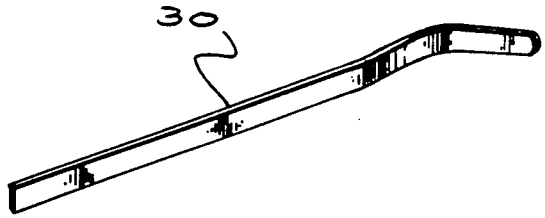

FIG. 4 is a perspective view of splint 12 of FIG. 1 with portions of the drawing being cut away to show two aluminum stays 30 and 32. As shown, the aluminum stays 30 and 32 are housed within the designated pockets 34 and 36, respectively, secured to sleeve 16. Normally, stays 30 and 32 support the front of the forearm, hand, fourth and fifth fingers. Stay 30, also shown in FIG. 6, is extended from approximately middle of the forearm to approximately middle of the hand to support the forearm and hand. As shown in FIG. 6, stay 30 is substantially flat throughout the length of the forearm, and is bent slightly as it passes over the pad of the thumb. In addition, stay 32 cooperates with stay 30 to provide further support for the front of the forearm. Stay 32, also shown in FIG. 5, also supports the hand, fourth and fifth fingers because it extends along the front of the forearm to the front of the fourth and fifth fingers. As shown in FIG. 5, stay 32 is substantially flat throughout the length of the forearm and is bent such that the fourth and fifth fingers cup around it. In summary, stays 30 and 32, in cooperation with sleeve 16, and straps 14, 18, and 20 firmly support the front of the forearm, hand, and fourth and fifth fingers.

Incidentally, concerning dimensions of the aluminum stays, they may be about ½ inch wide, 1/16 inch thick, and will vary in length from about 6 to 12 inches. These dimensions would vary, of course, depending on the material used and the size of the assembly.

It is to be understood that the foregoing description, and the embodiments shown in the drawings relate to illustrative embodiments of the invention. Various changes may be accomplished without departing from the spirit and scope of the invention. Thus, by way of example but not of limitation, the splint may include one or more stays; the stays may have various sizes and shapes; the stays may be made of aluminum or other appropriate metals, metal alloys, plastics, or other non-metals. The stays may be parallel to each other, or may be angled. Instead of aluminum stays, the splint may employ water activated or two component activated support means. The water activated support means is disclosed in related case, Ser. No. 198,152, filed May, 1988, and assigned to the assignee of this invention. When such water activated splinting arrangements are used, a front and a back water activated stay assembly could be employed, along with one or two aluminum stays to provide initial shape. Therefore, reference is made to this related case for a description of water activated support means. The splint may also employ a combination of aluminum stays and water activated support means. Further, the sleeve may have a vinyl surface or alternatively, it may have a surface made from other soft material. The sleeve may also include two portions that are connected together with a flexible hinge, or alternatively, it may have a single continuous portion. Finally, the sleeve may include more than two portions that are connected to each other using flexible hinges. Accordingly, the present invention is not limited to the embodiments precisely as shown or described hereinabove.

What is claimed is:

1. An orthopaedic soft goods splint assembly for immobilizing the wrist, the fourth and fifth fingers and outer portion of the hand, comprising:
    a flexible soft goods sleeve for at least partially enclosing the wrist, hand, and fourth and fifth fingers;
    splint means for substantially immobilizing the wrist, fourth and fifth fingers and outer portion of the hand, said splint means comprising support means for providing rigid support for the hand, wrist, and fourth and fifth fingers and outer portion of the hand, after said assembly is applied and bones are immobilized;
    fastening means for securely, removably, and adjustably fastening said sleeve to the wrist, hand and fingers, said fastening means contributing to the immobilization of the wrist, fourth and fifth fingers and outer portion of the hand; and
    means for securing said support means to said sleeve.

2. An orthopaedic splint assembly as defined in claim 1 wherein said support means includes at least one rigid stay.

3. An orthopaedic splint assembly as defined in claim 1 wherein said support means includes four rigid aluminum stays, namely, first, second, third, and fourth stays.

4. An orthopaedic splint assembly as defined in claim 3 wherein said first stay extends along said sleeve from the portion of said sleeve adjacent the middle of the forearm to the portion of said sleeve extending to the middle of the palm, said first stay being bent in the location where said sleeve is configured to pass over the pad at the base of the thumb when said splint assembly is mounted on a patient's forearm.

5. An orthopaedic splint assembly as defined in claim 3 wherein said second stay extends along said sleeve from the portion of said sleeve adjacent the middle of the forearm to the part of said assembly extending to the tips of the fourth and fifth fingers, said second stay being bent such that the fourth and fifth fingers, said second stay being bent such that the fourth and fifth fingers cupped around second stay when said splint assembly is mounted on patient's forearm.

6. An orthopaedic splint assembly as defined in claim 3 wherein said third stay extends along said sleeve from the area of said sleeve adjacent the back of the forearm to the part of said assembly extending to the back of the tips of the fourth and fifth fingers, said third stay being bent such that it securely holds the fingers cupped around said second stay; and
    wherein said fourth stay extends along the portion of said sleeve adjacent the back of the forearm and hand, said fourth stay being positioned opposite said first stay and being bent slightly over the back of the hand and ending at portion of said sleeve adjacent the middle of the hand, when said splint assembly is mounted on a patient's forearm.

7. An orthopaedic splint assembly as defined in claim 1 wherein said splint means includes at least two splint members, one extending along the portion of said sleeve adjacent the front of the wrist and hand, and the other extending along the portion of said sleeve adjacent the back of the wrist and hand, when said splint assembly is mounted on a patient's forearm.

8. An orthopaedic splint assembly as defined in claim 1 wherein said sleeve encompasses the wrist, fourth and fifth fingers, and the outer side of the hand, and wherein said assembly is generally U-shaped in cross-section, with the closed side of the U-shaped assembly engaging the fourth and fifth fingers and the outer side of the hand, wrist, and forearm.

9. An orthopaedic splint as defined in claim 3 wherein said sleeve comprises a first portion, a second portion and a flexible hinge, with said flexible hinge connecting said first and second portions.

10. An orthopaedic splint as defined in claim 9 wherein said first portion includes said first and second stays.

11. An orthopaedic splint as defined in claim 9 wherein said second portion includes said third and said fourth stays.

12. An orthopaedic splint as defined in claim 1 wherein said sleeve includes a vinyl covering.

13. An orthopaedic splint as defined in claim 1 wherein said fastening means includes a finger strap, a hand strap and forearm straps.

14. An orthopaedic splint as defined in claim 1 wherein said sleeve includes one type of securing material, said fastening means includes straps having a mating type of securing material for adjustably securing the straps to said sleeve, said securing material including a fine array of hooks and mating material with which said hooks can engage.

15. An ulna gutter orthopaedic soft goods splint assembly for immobilizing the wrist, the fourth and fifth fingers and the outer portion of the hand comprising:
   splint means for substantially immobilizing the wrist, hands, and fourth and fifth fingers, while leaving the thumb and index and middle fingers free, said splint means comprising rigid stays and providing support for the forearm, fourth and fifth fingers and the outer portion of the hand;
   a flexible soft goods sleeve for at least partially enclosing the forearm and the fourth and fifth fingers;
   fastening means for securely and adjustably fastening said splint to the wrist, hand and fingers, said fastening means contributing to the immobilization of the wrist, fourth and fifth fingers and the outer portion of the hand; and
   means for securing said rigid stays to said sleeve, and for providing padding between said stays and the forearm and fingers.

16. An orthopaedic splint as defined in claim 15 wherein said rigid support means includes four rigid stays, namely first, second, third, and fourth stay; said first stay extending from the middle of the forearm to the middle of the palm, said first stay being bent as it passes over the pad of the thumb; said second stay extending from the middle of the forearm to the tips of the fourth and fifth fingers, said second stay being bent such that the fourth and fifth fingers cup around said second stay; said third stay extending along the back of the forearm to the back of the tips of said fourth and fifth fingers, said third stay being bent such that it securely holds the fingers cupped around said second stay, and said fourth stay extending along the back of the forearm and hand, said fourth stay positioned opposite said first stay and bent slightly over the back of the hand and ending at the middle of the hand.

17. An orthopaedic splint as defined in claim 15 wherein said sleeve encompasses the wrist and fourth and fifth fingers and their radial aspects.

18. An orthopaedic splint as defined in claim 15 wherein said sleeve comprises a first portion, a second portion and a flexible hinge, with said flexible hinge connecting said first and second portions, said first portion including said first and second stays, said second portion includes said third and said fourth 19. An orthopaedic splint as defined in claim 15 wherein said fastening means includes a finger strap, a hand strap and forearm straps, said straps including one type of securing material, said sleeve including mating type of securing material on its surface, said straps adjustably securing said straps to said sleeve, said securing material including a fine array of hooks, and mating material with which said hook can engage.

20. An ulna gutter orthopaedic soft splint assembly for immobilizing the wrist, the fourth and fifth fingers, and the outer portion of the hand, comprising:
   a flexible soft goods sleeve for at least partially enclosing the forearm, fourth and fifth fingers, and outer portion of the hand;
   said assembly being generally U-shaped in cross-section with the closed side of the U-shaped assembly engaging the wrist, the fifth finger, and the outer portion of the hand;
   splint means for substantially immobilizing the wrist, fourth and fifth fingers and outer portion of the hand, said splint means comprising support means for providing rigid support for the forearm, fourth and fifth fingers and outer portion of the hand, after said assembly is applied and bones are immobilized;
   fastening means for securely, removably, and adjustably fastening said sleeve to the wrist, hand and fingers, said fastening means contributing to the immobilization of the wrist, fourth and fifth fingers and outer portion of the hand; and
   pocket means for securing said support means to said sleeve.

* * * * *